US00RE39609E

(19) United States
(12) Reissued Patent
Podos et al.

(10) Patent Number: US RE39,609 E
(45) Date of Reissued Patent: May 1, 2007

(54) 8-ISO-PROSTAGLANDINS FOR GLAUCOMA THERAPY

(75) Inventors: Steven M. Podos, Tenafly, NJ (US); Thomas W. Mittag, Pleasantville, NY (US); Bernard Becker, St. Louis, MO (US)

(73) Assignee: Mount Sinai School of Medicine of New York University, New York, NY (US)

(21) Appl. No.: 10/073,838

(22) Filed: Feb. 11, 2002

Related U.S. Patent Documents

Reissue of:
(64) Patent No.: 6,037,368
Issued: Mar. 14, 2000
Appl. No.: 09/073,552
Filed: May 6, 1998

U.S. Applications:

(63) Continuation of application No. 08/853,803, filed on May 9, 1997, now abandoned.

(51) Int. Cl.
*A61K 31/215* (2006.01)
*A61K 31/19* (2006.01)

(52) U.S. Cl. ..... 514/530; 514/573; 514/913
(58) Field of Classification Search ..... 514/530, 514/573, 913
See application file for complete search history.

(56) References Cited

U.S. PATENT DOCUMENTS 4,132,847 A * 1/1979 Kuhla et al. ..... 549/417
4,599,353 A * 7/1986 Bito ..... 514/530
5,151,444 A * 9/1992 Ueno et al. ..... 514/530
5,173,507 A * 12/1992 DeSantis et al. ..... 514/530
5,208,256 A * 5/1993 Ueno ..... 514/530
5,262,437 A * 11/1993 Chan ..... 514/530
5,462,968 A * 10/1995 Woodward ..... 514/568
5,476,872 A * 12/1995 Garst et al. ..... 514/530
5,565,492 A * 10/1996 DeSantis et al. ..... 514/530
5,578,618 A * 11/1996 Stjernschantz et al. ..... 514/365
5,631,287 A * 5/1997 Schneider ..... 514/530
6,124,353 A 9/2000 Woodward

FOREIGN PATENT DOCUMENTS

WO 9411002 * 5/1994

OTHER PUBLICATIONS

Podos et al., Mar. 15, 1998, Invest. Ophtalmol. Visual Sci. 39(4): S258, abstract 1178–B57, 1998.*

Wang et al., Mar. 15, 1997, Invest. Ophtalmol. Visual Sci. 38(4):S815, abstract 3795–B396.*

* cited by examiner

*Primary Examiner*—Zohreh Fay
(74) *Attorney, Agent, or Firm*—Dorsey & Whitney LLP

(57) ABSTRACT

The present invention relates to the use of 8-iso prostaglandins and their derivatives for decreasing intraocular pressure, for example in the treatment of glaucoma It is based, at least in part, on the discovery that 8-iso prostaglandin $E_2$ effectively decreased intraocular pressure by a trabecular meshwork outflow mechanism.

3 Claims, No Drawings

8-ISO-PROSTAGLANDINS FOR GLAUCOMA THERAPY

Matter enclosed in heavy brackets [ ] appears in the original patent but forms no part of this reissue specification; matter printed in italics indicates the additions made by reissue.

This application is a continuation of U.S. Ser. No. 08/853,803 *filed May 9, 1997* now abandoned.

INTRODUCTION

The present invention relates to the use of 8-iso prostaglandins and their derivatives for decreasing intraocular pressure, for example in the treatment of glaucoma. It is based, at least in part, on the discovery that 8-iso prostaglandin $E_2$ effectively decreased intraocular pressure by a trabecular meshwork outflow mechanism.

BACKGROUND OF THE INVENTION

Glaucoma is a major eye disease which can cause progressive loss of vision leading to blindness. The majority of human glaucomas are associated with increased intraocular pressure ("IOP") resulting from an imbalance in the rate of secretion of aqueous humor by the ciliary epithelium into the anterior and posterior chambers of the eye and the rate of aqueous humor outflow from these chambers, primarily via the canal of Schlemm. High IOP is considered the major risk factor for glaucomatous visual impairment resulting from the death of retinal ganglion cells, loss of the nerve fiber layer in the retina, and destruction of the axons of the optic nerve. Current treatments are directed toward reducing intraocular pressure.

Glaucoma is typically classified, on the basis of its etiology, as primary or secondary. Primary glaucoma in adults, a disorder in which the underlying cause is poorly understood, is associated with increased IOP due to an obstruction of aqueous human outflow. The obstruction may be caused by a blockage located at the angle formed between the iris and the lateral cornea, categorized as either open angle or acute or chronic angle closure. The anterior chamber of the eye appears normal in chronic open angle glaucoma, despite impaired drainage of aqueous humor. In contrast, the anterior chamber is shallow and the filtration angle is narrowed in chronic angle-closure glaucoma, wherein the trabecular meshwork and the canal of Schlemm may be obstructed by the iris. An acute attack of glaucoma may arise in this context when the pupil dilates, pushing the root of the iris forward to block the angle.

Secondary glaucoma is caused by another disorder which functionally interferes with the outflow of aqueous humor or the flow from the posterior to the anterior chamber. Such interference may be caused by inflammation, a tumor, an enlarged cataract, central retinal vein occlusion, trauma, or hemorrhage.

Several classes of drugs acting by different mechanisms are used as topically administered ocular therapy to lower IOP. These include beta adrenergic blockers (e.g., timolol), topical carbonic anhydrase inhibitors (e.g., dorzolamide), and alpha$_2$-adrenergic receptor agonists (e.g., clonidine derivatives), all of which act primarily by decreasing the formation of aqueous humor within the eye. Pilocarpine and epinephrine are clinical agents that also lower IOP in glaucamatous eyes, but these drugs act principally by decreasing the resistance in the trabecular meshwork outflow channels. A third mechanism for lowering IOP in the primate eye is by increasing the outflow of aqueous humor via the uveoscleral route. Recently, a prostaglandin derivative belonging to the F2α series of prostanoids, which acts primarily by this uveoscleral mechanism, has been introduced for glaucoma therapy. This drug, called latanoprost, is the isopropyl ester of a compound having the following structure:

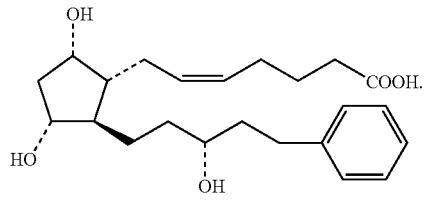

Prostaglandins which may be used in the treatment of glaucoma are described in U.S. Pat. Nos. 5,476,872 by Garst et al., 4,599,353 by Bito, 5,262,437 by Chan, 5,462,968 by Woodward, 4,132,847 by Kuhla, 5,173,507 by DeSantis et al., 5,578,618 by Stjernschantz et al., 5,208,256 by Ueno, 5,565,492 by DeSantis et al., 5,151,444 by Ueno et al., and PCT Application No. PCT/US93/10853, International Publication No. WO 94/11002 by Woodward.

The present invention relates to prostaglandins which are structurally different from latanoprost and other prostaglandins used in the treatment of glaucoma, and that belong to the 8-iso series of prostanoids, for example 8-iso $PGE_2$, 8-iso $PGE_2$ and 8-iso $PGF_{2\alpha}$. In contrast to latanoprost, 8-iso$PGE_2$ lowers IOP primarily by decreasing the resistance to trabecular outflow of aqueous humor from the eye.

SUMMARY OF THE INVENTION

The present invention relates to the use of 8-iso prostanoids in methods which decrease intraocular pressure ("IOP") in the eye, for example in the treatment of glaucoma. The 8-iso-prostanoids of the invention have a common structure according to formula I:

Formula I

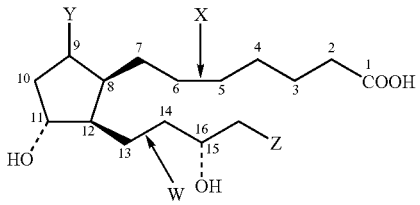

where either bond W or bond X can be a single or a double bond, Y is either (i) a hydroxyl group having either α or β orientation relative to the five-membered ring or (ii) a keto function at carbon 9, and Z is a hydrocarbon group which may be aliphatic (cyclic or non-cyclic), aromatic, or a combination of aliphatic and aromatic at carbon 16.

In a first nonlimiting embodiment of the invention, the 8-iso prostanoid is 8-iso prostaglandin $E_2$ (prosta-5,13-dien-1-oic acid, 11,15-dihydroxy-9-oxo, (5Z, 8β, 11α, 13E,15S), having Formula II:

Formula II

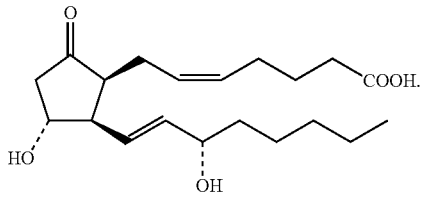

In a second nonlimiting embodiment of the invention, the 8-iso prostanoid is 8-iso, 5,6 dihydro prostaglandin $E_2$ (referred to as 8-iso $PGE_1$), having Formula II:

Formula III

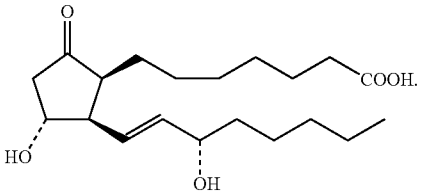

In a third nonlimiting embodiment of the invention, the 8-iso prostanoid is 8-iso $PGF_{2\alpha}$, (prosta-5,13-dien-1-oic acid, 9, 11, 15-trihydroxy-, (5Z, 8β, 9α, 11α, 13E, 15S)-, having Formula IV:

Formula IV

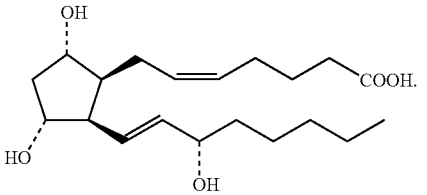

The present invention also provides for derivatives of compounds of Formulas II, III or IV which retain basic Formula I and their use in methods of decreasing intraocular pressure.

DETAILED DESCRIPTION OF THE INVENTION

The present invention relates to the use of 8-iso prostanoids having basic Formula I to decrease intraocular pressure in a subject in need of such treatment. In specific nonlimiting embodiments of the invention, the 8-iso prostanoid may be selected from the group of (i) 8-iso prostaglandin $E_2$ (prosta-5,13-dien-1-oic acid, 11,15-hydroxy-9-oxo, (5Z, 8β, 9α, 11α, 13E, 15S) ("8-iso $PGE_2$"), having Formula II; (ii) the 5,6 dihydro derivative of 8-iso $PGE_2$, having Formula III and referred to as 8-iso $PGE_1$; (iii) prosta-5,13-dien-1-oic acid, 9, 11, 15-trihydroxy-, (5Z, 8β, 9α, 11α, 13E, 15S) ("8-iso $PGF_{2\ \alpha}$"), having Formula IV; and (iv) derivatives of compounds having Formulas II, III or IV which retain basic Formula I and which, when administered to the eye of a subject having increased intraocular pressures, will decrease intraocular pressure by at least 10 percent.

The main structural differences between the 8-iso prostanoids of the invention and latanoprost are the following: (i) the side chain substituents on the five-membered rings have the opposite geometric arrangement with respect to the plane of the ring (cis for the 8-iso prostanoids of the invention and trans for latanoprost); (ii) the five-membered ring has a keto or hydroxyl function at position 9 in the 8-iso prostanoids of the invention, whereas there is just a hydroxyl group in the same position in latanoprost; and (iii) the side chains beginning with the sixteenth carbon may have different structures, as, for example, latanoprost containing a terminal methyl phenyl group at this position. 8-iso prostanoid derivatives of the invention contain a five-membered ring and two side chains, and retain distinguishing features (i)–(iii) as set forth in the preceding sentence and in Formula I. In preferred embodiments, such derivatives are esters of compounds having Formula II, III or IV. For example, esterified derivatives of 8-iso $PGE_2$ may be used according to the invention, and may provide improved penetration into the eye.

The mechanism of action by which 8-iso $PGE_2$ lowers IO has been found to be different from that of latanoprost in experiments done in primates, in that 8-iso $PGE_2$ has been found to increase trabecular outflow facility by decreasing resistance to outflow of aqueous humor. This is an advantage in that the trabecular meshwork is the primary locus of the pathology causing increased IOP in primary open angle glaucoma.

Accordingly, the present invention provides for a method for decreasing IOP comprising administering a therapeutically effective amount of an 8-iso prostanoid of the invention to a subject in need of such treatment. Such a method may be used in the treatment of glaucoma in a subject. Suitable formulations include for example, and not by way of limitation, a topical solution which is a physiological saline solution, having a pH between about 4.5 and 8 and an appropriate buffer system (e.g., acetate buffers, citrate buffers, phosphate buffers, borate buffers) a neutral pH being preferred. The formulation may further comprise a pharmaceutically acceptable preservative (e.g. benzalkonium chloride, thimerosol, chlorobutanol), stabilizer and/or surfactant (e.g. Tween 80). The formulation may also comprise a compound which acts as an anti-oxidant (e.g. sodium metabisulfite, sodium thiosulfate, acetylcysteine, butylated hydroxyanisole, butylated hydroxytoluene). A "therapeutically effective amount" of an 8-iso prostanoid of the invention refers to an amount of drug which decreases the IOP by at least about 10 percent, preferably at least about 15 percent, and more preferably at least about 20 percent. In particular embodiments of the invention, the administration of 8-iso prostanoid results in an increase in trabecular outflow facility of at least about 10 percent, preferably at least about 20 percent, and more preferably at least about 30 percent. In nonlimiting embodiments of invention, a topical preparation of 8-iso prostanoid at a concentration of between 0.001 and 1 percent, preferably between 0.05 and 0.2 percent, and more preferably between about 0.05 and 0.1 percent may be used.

According to the invention, IOP may be decreased, and/or glaucoma may be treated, using compositions comprising an 8-iso prostanoid of the invention as the sole active agent, or in conjunction with another active agent. For example, combination of 8-iso prostanoid and another drug used to treat elevated intraocular pressure, including but not limited to another prostaglandin derivative (including, but not limited to, latanoprost), pilocarpine, epinephrine, a beta adrenergic agent (e.g., timolol), a carbonic anhydrase inhibitor (e.g., dorzolamide), or an $alpha_2$-adrenergic receptor agonist (e.g., a clonidine derivative), may be used.

EXAMPLE 1

Experiments were performed to evaluate the effects of single dose administration of 8-iso $PGE_2$ an IOP in normal ("N") and glaucomatous ("G") monkey eyes, and to determine the mechanism by which 8-iso $PGE_2$ alters IOP in N monkey eyes, when applied topically. A single 25 μl dose study was performed in 6 N and 8 G monkeys. IOP and pupil sizes were measured before and at 0 hr, 0.5 hr and then hourly for a total of 6 hrs after 0.05% or 0.1% drug concentrations were administered. Tonographic outflow facility ("C") and fluorophotometric aqueous humor flow (F) were determined in 6 N monkeys before and after unilateral application of 25 μl of 0.1% 8-iso $PGE_2$. In 8 G monkey eyes, 8-iso$PGE_2$ reduced IOP ($p<0.005$) up to 2 hrs or 5 hrs following administration of the 0.05% or 0.1% concentration, respectively. The maximum reduction in IOP was 4.6±0.8 (mean±SEM)mm Hg (0.05%) and 6.6±0.8 mm Hg (0.1%), as compared to baseline measurements. After topical application of 8-iso $PGE_2$ the IOP was lower ($p<0.01$) in the treated eyes of 6 N monkeys for 4 hrs, with a maximum difference of 3.2±0.2 mmHg, as compared to the fellow contralateral control eyes. The pupil size was smaller ($p<0.01$) for 4 hrs, up to 1.0±0.2 mm. Compared with vehicle-treated contralateral control eyes, C was greater ($p<0.005$) by 48% at 2 hr after a single dose of 0.1% 8-iso $PGE_2$. F was unchanged ($p<0.10$) over a period of 4 hrs after drug administration. Mild eyelid edema, conjunctival edema, hyperemia, and discharge appeared in some eyes treated with the 0.1% concentration.

Table 1A shows that 8-iso $PGE_2$ administrated to the normal monkey eye lowers IOP significantly by 20.3% and increases outflow facility by 43.1%, an amount sufficient to account for the fall of IOP. By contrast, in Table 1B latanoprost in the normal monkey eye also lowers IOP significantly (by 10.8%), but the drug has not significant effect on outflow facility. The lack of a major effect on outflow facility of latanoprost in the primate eye is in agreement with studies in the literature by other investigators.

TABLE 1

A. Effect of 0.1% 8-iso$PGE_2$ on Outflow Facility in 6 Normal Monkeys (2 hours after treatment)

| | Intraocular Pressure Mean ± SEM mmHg | Outflow Facility Mean ± SEM μl/ml/mmHg |
|---|---|---|
| Treated eyes (drug) | 13.0 ± 0.7* | 0.83 ± 0.10* |
| Baseline | 16.3 ± 1.1 | 0.58 ± 0.03 |
| Control eyes (vehicle) | 15.7 ± 0.5 | 0.56 ± 0.06 |
| Baseline** | 15.7 ± 0.6 | 0.51 ± 0.04 |

B. Effect of 0.005% latanoprost on Outflow Facility in 6 Normal Monkeys (1 hour after treatment)

| | Intraocular Pressure Mean ± SEM mmHg | Outflow Facility Mean ± SEM μl/min/mmHg |
|---|---|---|
| Treated eyes (drug) | 13.2 ± 0.7* | 0.76 ± 0.08 |
| Baseline | 14.8 ± 0.7 | 0.62 ± 0.07 |
| Control eyes (vehicle) | 15.0 ± 0.8 | 0.60 ± 0.07 |
| Baseline** | 15.7 ± 0.3 | 0.73 ± 0.08 |

*Significantly different as compared with either baseline values or vehicle-treated eyes (two-tailed paired t-test, p. < 0.05.
**Baseline measurements made in the same monkeys at the same time one day prior to drug treatments Table 2 shows the effect of 8-iso $PGE_2$ on IOP and outflow facility in glaucomatous monkey eyes. Because of the individual variability in laser-induced glaucomatous monkey eyes, the IOP and facility measurements are expressed in the table as ratios (value of the drug-treated eye+the value of the vehicle-treated eye). The ratios were calculated from the values of the same glaucomatous monkey eye determined immediately prior to administration of the drug or the vehicle (time 0 hrs.), and the values at 2 hours after administration of the drug or vehicle. The data in Table 2 show that in the primate, administration of 8-iso $PGE_2$ to glaucomatous eyes significantly lowers IOP (by 13.8%) and significantly increases outflow facility (by 38.8%), which is of sufficient magnitude to account for the fall in IOP. Thus the mechanism of lowering IOP by 8-iso $PGE_2$ in both normal and glaucomatous eyes is primarily due to an increase in aqueous humor trabecular outflow.

TABLE 2

Effect of 0.1% 8-iso $PGE_2$ on IOP Outflow Facility Responses in 8 Glaucomatous Monkey Eyes (Unilateral)

| | Intraocular Pressure (drug-treated/ vehicle-treated) | | Outflow facility (drug-treated/ vehicle treated) | |
|---|---|---|---|---|
| Time | 0 hr | 2 hr | 0 hr | 2 hr |
| Response Ratio (±SEM) | 0.976 ± 0.002 | 0.843* ± 0.0498 | 1.041 ± 0.0498 | 1.445** ± 0.161 |
| % Change by drug | — | 13.8% decrease | — | 38.8% decrease |

Significantly different as compared to 0 hr, paired t-test, $p < 0.01$*, <0.10**

EXAMPLE II

IOP was measured one hour before and at intervals up to six hours after a single dose of 8-iso PGE, (the 13, 14 dihydro derivative of 8-iso $PGE_2$), 8-iso $PGE_2$, or 8-iso $PGF_{2\alpha}$ in laser-induced glaucomatous eyes in cynomolgus monkeys (wherein only one eye is rendered glaucomatous and the other serves as a control). Following one day of baseline IOP measurement, a single 25 μl dose of either (i) 0.1 percent 8-iso $PGE_1$, or (ii) 0.1 percent 8-iso $PGE_2$, or (iii) 0.1 percent 8-iso $PGF_{2\alpha}$, was topically applied to the glaucomatous eye in groups of 4 or 8 monkeys. It was found that 8-iso $PGE_1$ (0.1 percent) reduced IOP ($p<0.05$) for up to four hours in glaucomatous monkey eyes (n=4). The maximum reduction in IOP was 5.3±0.8 (mean SEM) mm Hg at 2 hours after dosing 8-iso $PGE_2$ (0.1 percent) reduced IOP ($p<0.05$) for 5 hours with a maximum reduction in IOP of 6.6±0.8 mm Hg at 2 hours after dosing (n=8). After 0.1 percent 8-iso $PGF_{2\alpha}$, a significant ($p<0.05$) reduction in IOP occurred only at 1 hour with the maximum reduction in IOP of 3.3±0.9 mm Hg (n=4). The results are shown in Table 3. Based on these studies, of the compounds tested, 8-iso $PGE_2$ appears to have the greatest and 8-iso $PGF_{2\alpha}$, the least activity in decreasing IOP in glaucomatous monkey eyes.

TABLE 3

Intraocular Pressure (treated - baseline) (mean mm Hg ± SEM)

| iso PG, 0.1% | n | 1 hr | 2 hr | 4 hr | 6 hr |
|---|---|---|---|---|---|
| 8-iso $PGE_1$ | 4 | −3.3 ± 1.3 | −5.3 ± 0.8* | −2.3 ± 0.5* | −1.3 ± 0.9 |
| 8-iso $PGE_2$ | 8 | −4.5 ± 0.9** | −6.6 ± 0.8** | −2.9 ± 0.6** | −1.2 ± 1.2 |
| 8-iso $PGE_{2\alpha}$ | 4 | −3.3 ± 0.8* | −1.8 ± 1.1 | −0.8 ± 1.7 | 0.3 ± 0.5 |

*$p < 0.05$
**$p < 0.005$

Various publications are cited herein, the contents of which are hereby incorporated by reference in their entireties.

We claim:

[1. A method for decreasing intraocular pressure comprising administering a therapeutically effective amount of an 8-iso prostanoid having the following Formula I:

Formula I

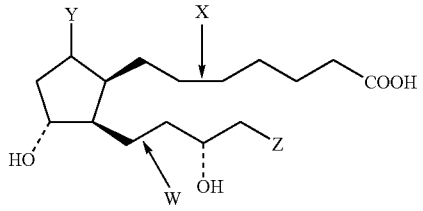

where bond W is selected from the group consisting of a single covalent bond and a double covalent bond, bond X is selected from the group consisting of a single covalent bond and a double bond, substituent Y is selected from the group consisting of a hydroxyl group having either α or β orientation relative to the five-membered ring and a keto function, and substituent Z is a hydrocarbon group selected from the group of aliphatic, aromatic, or a combination of aliphatic and aromatic hydrocarbon, to a patient in need of such treatment.]

[2. The method of claim 1 wherein the 8-isoprostanoid is administered topically.]

[3. The method of claim 2 wherein the 8-iso prostanoid is administered as a composition comprising between 0.005 to 1 percent 8-iso prostanoid.]

[4. The method of claim 1, wherein the 8-iso prostanoid is selected from the group consisting of a compound having the following Formula II Formula II

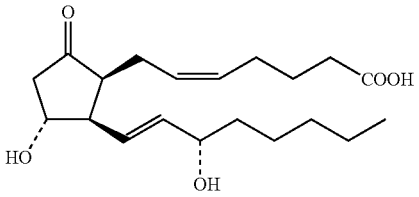

or a derivative thereof.]

[5. The method of claim 1, wherein the 8-iso prostanoid is selected from the group consisting of a compound having the following Formula III Formula III

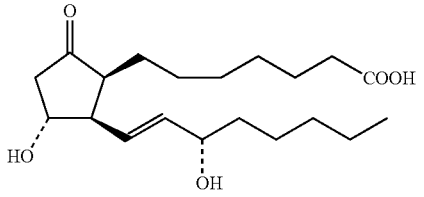

or a derivative thereof.]

[6. The method of claim 1, wherein the 8-iso prostanoid is selected from the group consisting of a compound having the following Formula IV Formula IV

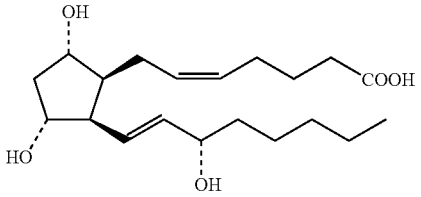

or a derivative thereof.]

[7. The method of claim 2, wherein the 8-iso prostanoid is selected from the group consisting of a compound having the following Formula II Formula II

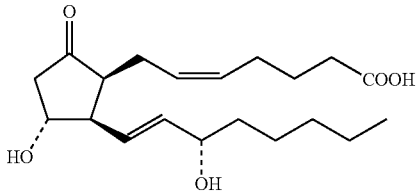

or a derivative thereof.]

[8. The method of claim 2, wherein the 8-iso prostanoid is selected from the group consisting of a compound having the following Formula III Formula III

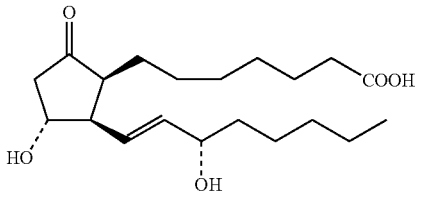

or a derivative thereof.]

[9. The method of claim 2, wherein the 8-iso prostanoid is selected from the group consisting of a compound having the following Formula IV Formula IV

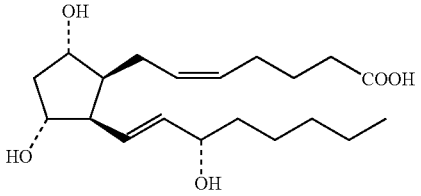

or a derivative thereof.]

[10. The method of claim 3, wherein 8-iso prostanoid is selected from the group consisting of a compound having the following Formula II Formula II

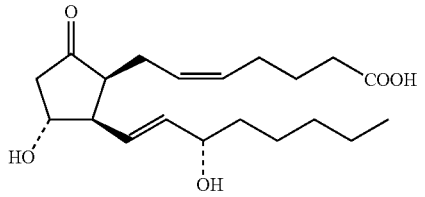

or a derivative thereof.]

[11. The method of claim 3, wherein the 8-iso prostanoid is selected from the group consisting of a compound having the following Formula III Formula III

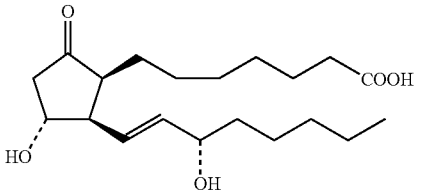

or a derivative thereof.]

[12. The method of claim 3, wherein the 8-iso prostanoid is selected from the group consisting of a compound having the following Formula IV Formula IV

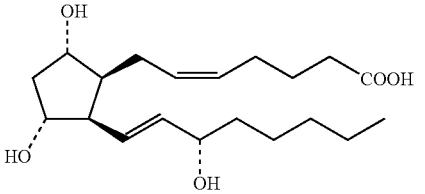

or a derivative thereof.]

[13. The method of claim 4, wherein the derivative is an ester derivative.]

[14. The method of claim 5, wherein the derivative is an ester derivative.]

[15. The method of claim 6, wherein the derivative is an ester derivative.]

[16. The method of claim 7, wherein the derivative is an ester derivative.]

[17. The method of claim 8, wherein the derivative is an ester derivative.]

[18. The method of claim 9, wherein the derivative is an ester derivative.]

[19. The method of claim 10, wherein the derivative is an ester derivative.]

[20. The method of claim 11, wherein the derivative is an ester derivative.]

[21. The method of claim 12, wherein the derivative is an ester derivative.]

*22. A method for decreasing intraocular pressure comprising administering a therapeutically effective amount of an 8-iso prostanoid having the following Formula I:*

*Formula I*

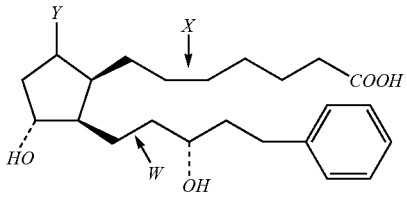

*where bond W is selected from the group consisting of a single covalent bond and a double covalent bond, bond X is selected from the group consisting of a single covalent bond and a double covalent bond and substituent Y is selected from the group consisting of a hydroxyl group having either α or β orientation relative to the five-membered ring and a keto function, to a patient in need of such treatment.*

*23. The method of claim 22 wherein the 8-iso prostanoid is administered topically.*

*24. The method of claim 22 wherein the 8-iso prostanoid is administered as a composition comprising between 0.005 to 1 percent 8-iso prostanoid.*

* * * * *